(12) United States Patent
Dolgin et al.

(10) Patent No.: US 6,327,504 B1
(45) Date of Patent: Dec. 4, 2001

(54) TRANSCUTANEOUS ENERGY TRANSFER WITH CIRCUITRY ARRANGED TO AVOID OVERHEATING

(75) Inventors: Alexander Dolgin, Lexington, MA (US); Thomas C. Rintoul, Gold River, CA (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 09/567,942

(22) Filed: May 10, 2000

(51) Int. Cl.[7] .................................................. A61N 1/02
(52) U.S. Cl. ........................................................ 607/61
(58) Field of Search ........................................ 607/61, 33

(56) References Cited

U.S. PATENT DOCUMENTS

| | | |
|---|---|---|
| 4,096,866 | 6/1978 | Fischell . |
| 4,143,661 | 3/1979 | LaForge et al. . |
| 4,432,363 | 2/1984 | Kakegawa . |
| 4,441,498 | 4/1984 | Nordling . |
| 4,665,896 | 5/1987 | LaForge et al. . |
| 5,109,843 | 5/1992 | Melvin et al. . |
| 5,193,539 | 3/1993 | Schulman et al. . |
| 5,193,540 | 3/1993 | Schulman et al. . |
| 5,279,292 | 1/1994 | Baumann et al. . |
| 5,314,453 | 5/1994 | Jeutter . |
| 5,350,413 | 9/1994 | Miller . |
| 5,591,217 | 1/1997 | Barreras . |
| 5,690,693 | 11/1997 | Wang et al. . |
| 5,702,430 | 12/1997 | Larson, Jr. et al. . |
| 5,702,431 | 12/1997 | Wang et al. . |
| 5,713,939 | 2/1998 | Nedungadi et al. . |
| 5,715,837 | 2/1998 | Chen . |
| 5,733,313 | 3/1998 | Barreras, Sr. et al. . |
| 5,741,316 | 4/1998 | Chen et al. . |
| 5,749,909 | 5/1998 | Schroeppel et al. . |
| 5,755,748 | 5/1998 | Borza . |
| 5,769,877 | 6/1998 | Barreras, Sr. . |
| 5,807,397 | 9/1998 | Barreras . |
| 5,876,425 | 3/1999 | Gord et al. . |
| 5,891,183 | 4/1999 | Zierhofer . |
| 5,945,762 | 8/1999 | Chen et al. . |
| 5,948,006 | 9/1999 | Mann . |

OTHER PUBLICATIONS

Burke et al., "HeartMate II: Design and Development of a Fully Implantable Axial Flow LVAS," 8th Congress of the International Society for Rotary Blood Pumps, Sep. 6–9, 2000, Aachen, Germany.

*Primary Examiner*—Scott M. Getzow
(74) *Attorney, Agent, or Firm*—Fish & Richardson P.C., P.A.

(57) ABSTRACT

A device, system and method for transcutaneous energy transfer (TET). Implanted circuitry suitable for conditioning the power delivered transcutaneously may be constructed in planar fashion, may be located in or near an implanted coil, and may be oriented such that the plane of the circuitry is substantially tangent to the lines of magnetic flux. The orientation of the circuitry may reduce eddy currents and their potentially harmful effects.

28 Claims, 4 Drawing Sheets

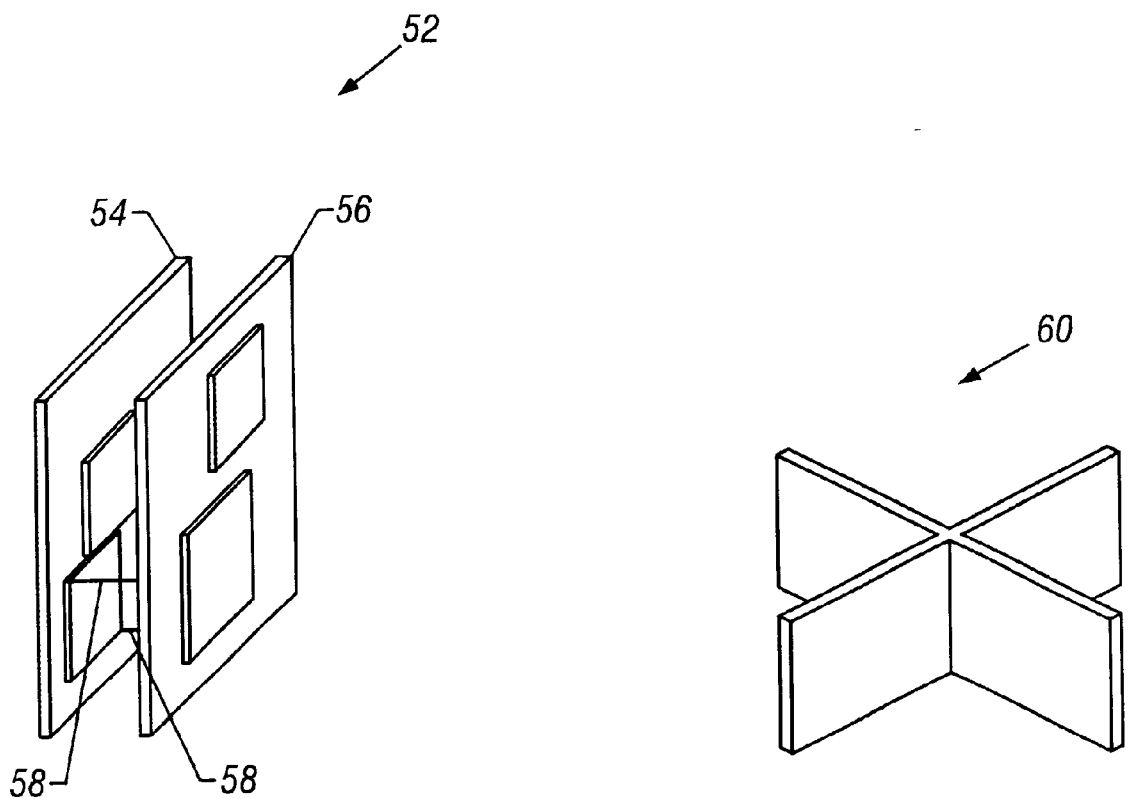
FIG. 4
FIG. 5
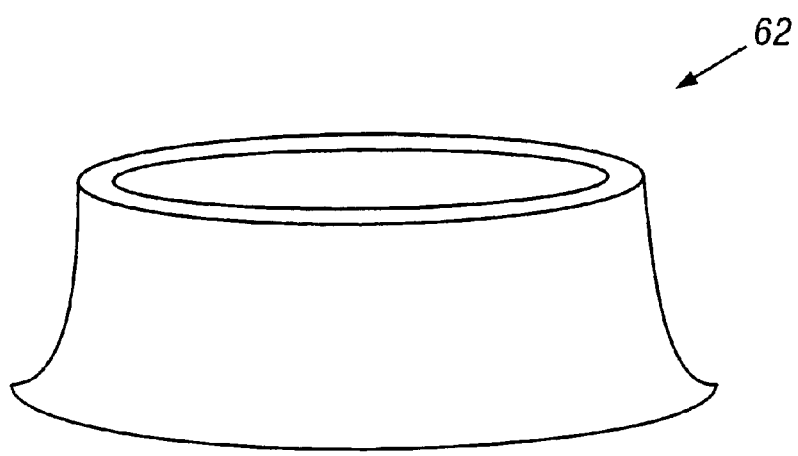
FIG. 6

TRANSCUTANEOUS ENERGY TRANSFER WITH CIRCUITRY ARRANGED TO AVOID OVERHEATING

TECHNICAL FIELD

The invention relates to the transfer of electromagnetic energy between a primary coil located outside the skin and a secondary coil located beneath the skin. More specifically, the invention concerns the circuitry used in connection with the secondary coil to condition the electromagnetic energy into a useful form.

BACKGROUND

Many implanted medical devices are powered by electricity. Some devices, such as artificial pacemakers, may be battery-powered because their power requirements are comparatively low. Other devices require considerably more power and cannot be adequately supplied by a battery on a long-term basis. An implantable blood pump, for example, requires considerably more power than an ordinary pacemaker. A pacemaker rhythmically generates electrical impulses to stimulate the heart muscle, but the pacemaker does not perform any mechanical pumping action. An implantable blood pump, by contrast, mechanically assists the heart muscle to pump blood, and for this reason has a considerably greater power requirement.

Power requirements for a typical pacemaker may be on the order of 10 milliwatts, as compared with an implantable blood pump, which may have a power requirement one thousand times greater. Implantable electric storage batteries are unable to provide such power for long periods of time, and the frequent invasive surgery that would be required to replace the batteries makes this option undesirable. If the implantable batteries are rechargeable, then the batteries must be recharged from time to time, and power must in some way be delivered to recharge the batteries. Once again, use of invasive surgery to deliver the recharge is not a desirable alternative.

Ordinarily the power source for a high-power device must be external to the body. To deliver the power to the device, the power must somehow transit through the skin. Power may be delivered through the skin by a percutaneous wire, but this method has drawbacks. A wire penetrating the skin provides a source for infection. Moreover, there is a risk that a wire penetrating the skin may accidentally be torn out, which may cause loss of power to the device and trauma to the patient.

Another way to deliver power through the skin is by way of induction. Two coils of electrically conductive wire, a primary coil external to the skin and a secondary coil implanted within the patient, may be inductively coupled. By energizing the primary coil with a time-varying current, a time-varying magnetic flux is produced by the primary coil. If the secondary coil is in proximity to the primary coil and is appropriately oriented, the time-varying magnetic flux will induce a time-varying current within the secondary coil, according to the principle of mutual induction. Power may be delivered through the skin using mutual induction. Systems delivering energy or power in this way are often called transcutaneous energy transfer, or TET, systems, sometimes referred to as TETS.

Mutual induction is a consequence of Faraday's Law of Induction. Faraday's Law holds that the electromotive force (emf) in a conducting coil of N turns and the rate of change of magnetic flux through the coil are related. Faraday's Law is embodied within the equation $E=-N(d\Phi/dt)$, where E is the induced emf, N is the number of turns in the coil, and $(d\Phi/dt)$ represents the change in magnetic flux with respect to time. The negative sign is a matter of convention, and is indicative of the direction of the induced emf.

Both the current in the primary coil and the current induced in the secondary coil are time-varying. Direct current (dc) will not result in a time-varying magnetic flux, and therefore will not create mutual induction. If the device being powered operates using dc, the current or voltage in the secondary coil must be conditioned for use by the device. Ordinarily, conditioning includes such functions as rectifying the current or voltage, filtering it to remove high-frequency components, and regulating it to provide substantially constant amounts of current or voltage.

SUMMARY

The present invention is directed to a transcutaneous energy transfer system having a secondary coil with integrated power conditioning circuitry. The transcutaneous energy transfer system may be particularly useful with an implantable blood pump having a pump control module. The pump control module ordinarily is implanted in the abdomen. Integration of the power conditioning circuitry with the secondary coil permits immediate conversion of energy induced at the secondary coil to dc current, instead of at the pump control module. Consequently, thinner leads can be used to couple the secondary coil to the pump control module, thus enhancing system versatility by expanding sites available for module implantation.

Importantly, the secondary coil and power conditioning circuitry can be arranged to provide a relatively low profile for implantation, while also limiting the generation of eddy currents in the power conditioning circuitry. Eddy currents in the power conditioning circuitry may be created when the circuitry is in proximity to the time-varying magnetic flux generated by the primary coil. A reduction in the generation of eddy currents helps avoid the creation of excessive heat in the area of the secondary coil, and resulting inflammation of nearby tissue. In particular, the power conditioning circuitry can be mounted within the aperture defined by the secondary coil with a structure and orientation designed to avoid coincidence with magnetic flux lines extending substantially perpendicular to the major plant defined by the secondary coil.

Ordinarily, power-conditioning circuitry is constructed as a substantially planar package or module. The circuitry may be placed on one or more circuit boards mounted within the aperture defined by the secondary coil and may be electrically connected to the secondary coil such that time-varying currents induced in the secondary coil are delivered to the conditioning circuitry. Although the conditioning circuitry may be encased in a non-conductive medium, the conditioning circuitry and circuit board may consist of conductors and semiconductors. To reduce the profile of the secondary coil, the planar circuitry is oriented to reside within the coil aperture and occupy the major plane defined by the coil.

Placement of the conditioning circuitry inside the secondary coil may have significant space-saving advantages, but may pose practical difficulties. The time-varying magnetic flux generated by the primary coil ordinarily will induce some time-varying eddy currents, in addition to the current induced within in the secondary coil. These induced eddy currents may appear in conductors and semiconductors in the power conditioning circuitry near the secondary coil. Eddy currents generate heat, due to the natural and inherent resistivity of the conductors.

The present invention provides a way for the circuitry to be mounted within the secondary coil yet minimize eddy currents and thereby reduce the risk of excessive heating. TET systems may be in many forms, and the orientation of the lines of magnetic flux may be estimated. Where the primary and secondary coils are substantially circular and are axially aligned, for example, the location lines of magnetic flux can be reasonably estimated, especially along the diameters and near the centers of the coils.

The present invention provides that the circuitry attendant to the secondary coil may be substantially planar, and may be placed so that the plane of the circuitry is substantially tangent to the lines of magnetic flux. In general, the lines of magnetic flux may pass through the major plane of the secondary coil at near-right angles, and magnetic flux lines near the center of the secondary coil's aperture may be substantially parallel to the secondary coil's axis.

When the planar circuitry is oriented with its plane substantially tangent to the lines of magnetic flux, eddy currents within the conductors and semiconductors in the circuitry are reduced. In one aspect, the present invention generally provides a device for use in transcutaneous energy transfer, comprising a coil for subcutaneous placement, and substantially planar circuitry electrically connected to the coil, wherein the plane of the circuitry is oriented substantially tangent to the lines of magnetic flux. In preferred embodiments, the plane of the circuitry preferably is oriented substantially perpendicular to the major plane of the coil to minimize creation of eddy currents within the circuitry.

To reduce the vertical profile of the circuitry relative to the major plane of the coil, the circuitry can be divided into sub-planes that are mounted adjacent one another in a stacked relationship. For example, the circuitry may include two or more circuit planes with surface-mounted components that form a multi-plane circuit package, e.g., a "double-decker" or "triple-decker" arrangement. Alternatively, the circuit package may provide multiple interlocking circuit planes.

In either case, the electrical components necessary for conditioning are distributed among two or more circuit planes, which may be individual printed circuit board sections. As a further alternative, the circuitry may take on a curved shape. In this manner, the surface area and resulting height of each board section within the coil aperture can be reduced to thereby reduce the profile of the coil for implantation.

In general, the present invention provides a device for use in transcutaneous energy transfer, comprising a coil for subcutaneous placement within a human, and circuitry that is electrically connected to the coil, configured to conduct current induced in the coil. A major plane of the circuitry is oriented substantially perpendicular to a major plane of the coil, thereby reducing the generation of eddy currents within the circuitry while current is conducting in the coil.

The circuitry may be located within the aperture of the coil. The circuitry may include substantially planar subcircuits, the planes of the subcircuits substantially located perpendicular to the major plane of the coil. Where the lines of magnetic flux are principally generated by a primary coil external to the skin, the substantially planar circuitry may be oriented substantially tangent to the lines of magnetic flux.

In another aspect, the invention provides a TET system. The system comprises a primary coil for placement external to the skin, the coil suitable for carrying a time-varying current, and a current source arranged in series with the primary coil, comprising a power supply and power circuitry capable of delivering an electric current to the primary coil to produce magnetic flux. The system further comprises a secondary coil for subcutaneous placement, suitable for carrying a current induced by the magnetic flux.

The system further comprises substantially planar conditioning circuitry that is electrically connected to the secondary coil and conducts current induced in the secondary coil, wherein the plane of the conditioning circuitry is oriented substantially perpendicular to the a major plane of the secondary coil. The system may further include a subcutaneous electrical device, connected to the conditioning circuitry by one or more leads.

In a further aspect, the invention provides a TETS method. The method comprises placing a primary coil external to the skin, the primary coil being electrically coupled to a power supply capable of delivering time-varying current to the primary coil. The method further comprises determining the orientation of magnetic flux lines principally caused by time-varying current circulating in the primary coil in proximity to a secondary coil that will be placed beneath the skin. The method further includes constructing conditioning circuitry in substantially planar fashion, and orienting the plane of the conditioning circuitry so it will be substantially tangent to the lines of magnetic flux.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 4 is a perspective view of a substantially planar circuitry arrangement in accordance with an embodiment of the invention.

FIG. 5 is a perspective view of a substantially planar circuitry arrangement in accordance with an embodiment of the invention.

FIG. 6 is a perspective view of a substantially planar yet curved circuitry arrangement in accordance with an embodiment of the invention.

DESCRIPTION

Figure 1:
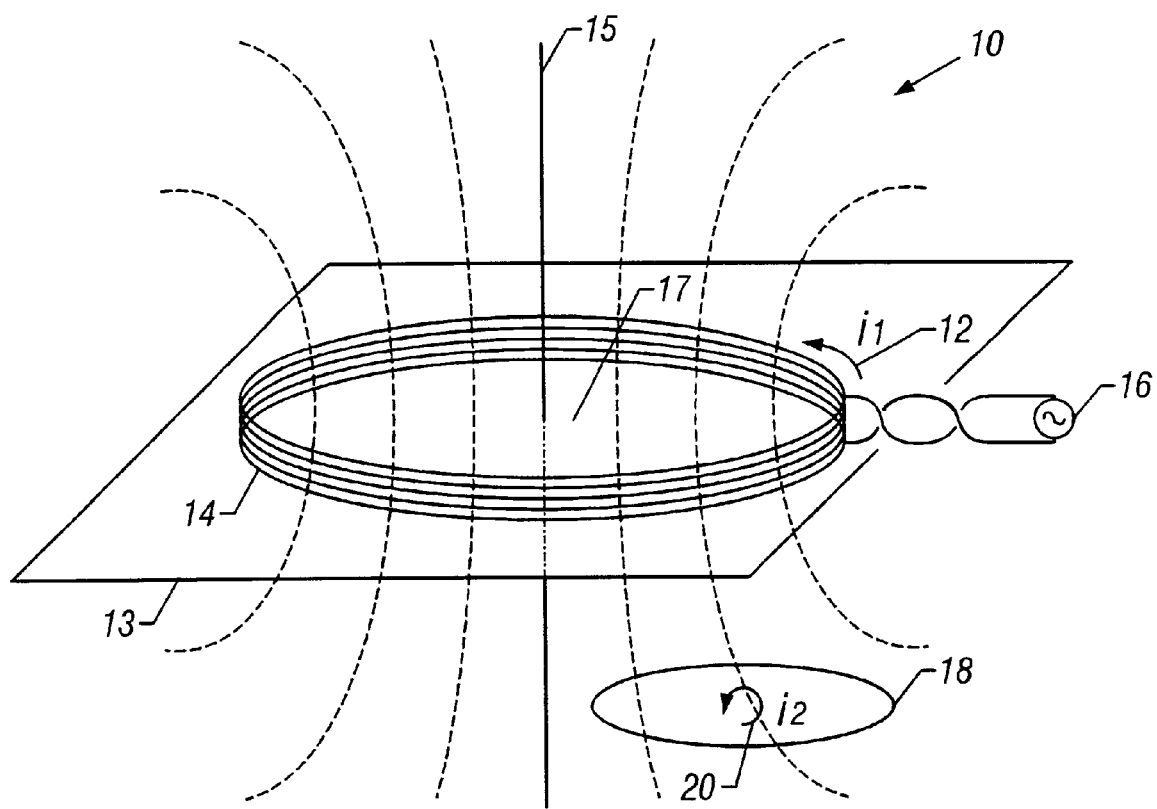
FIG. 1 is a simplified conceptual diagram of a coil and magnetic flux lines.

FIG. 1 is a conceptual diagram depicting magnetic flux lines 10 generated when a time-varying current i1 (12) circulates in a closely-wound coil 14. Coil 14 comprises at least one turn of electrically conductive wire. A closely-wound coil has multiple turns, and ordinarily has the turns closely-packed such that the magnetic flux through each turn is virtually the same. For ease of representation, coil 14 is not depicted in FIG. 1 as closely-wound. FIG. 1 shows coil 14 with a substantially circular perimeter. The turns of coil 14 define a center opening or aperture 17. Coil 14 also defines an axis 15 through the center of aperture 17, perpendicularly intersecting major coil plane 13. The turns of coil 14 lie substantially in major coil plane 13. Other coils described below may have an aperture, axis and major coil plane, which may be defined in a similar manner.

Time-varying current i1 (12) is generated by a current source 16. According to the Biot-Savart Law, a magnetic field is created by a current-carrying conductor. Time-varying current i1 (12) circulating in coil 14 causes coil 14 to behave like a magnetic dipole, with a corresponding magnetic field represented by magnetic flux lines 10. As current i1 (12) varies with time, magnetic flux lines 10 vary with time as well. As shown in FIG. 1, where the lines of magnetic flux 10 pass through the major coil plane 13, the lines of magnetic flux 10 are essentially perpendicular to the major coil plane 13. In addition, magnetic flux lines 10 near the center of aperture 17 are substantially parallel to the axis 15 of coil 14.

A thin, planar conductor 18 is depicted in FIG. 1 as near coil 14, and some of the magnetic flux lines 10 pass through the surface of conductor 18. The time-varying magnetic flux 10 may induce time-varying electromotive forces and time-varying currents within conductor 18, according to Faraday's Law and Lenz's Law. Such time-varying currents may be referred to as "eddy currents." In FIG. 1, current i2 (20) is one of theoretically many eddy currents circulating within conductor 18. The shape and direction of the path of eddy current i2 (20) shown in FIG. 1 are arbitrary. The actual shape and direction of the eddy currents may be affected by the local shape and strength of the magnetic flux, and by whether the flux is locally increasing or decreasing.

In some circumstances, eddy currents may have a number of undesirable effects. For example, eddy currents produce their own time-varying magnetic fields, which may interfere with the operation of other nearby electrical or electronic elements. Also, ordinary (non-superconducting) conductors have inherent resistance to currents flowing in the conductors, and convert some of the electrical energy of eddy currents into thermal energy, or heat. Generation of excess heat may be especially detrimental in circumstances where circuitry may burn out, or in circumstances where the heat is sufficiently intense to cause a burn or other trauma to a patient's tissue. Furthermore, eddy currents generally represent an undesirable waste of energy.

Eddy currents generally exist perpendicular to magnetic flux lines and depend upon the magnitude of magnetic flux flowing through the conductor. The magnetic flux is represented by flux lines 10. Flux lines 10 passing through coil 14 are curved, but the flux lines intersect the coil's major plane 13 at substantially right angles. Flux lines 10 passing through conductor 18 can be broken down into two components: a tangent component parallel to the surface of conductor 18, and a normal component perpendicular to the surface of conductor 18. Eddy current i2 (20) is perpendicular to the normal components of the flux lines. In general, the smaller the normal components of the flux lines passing through the conductor, the smaller the induced eddy currents within the conductor. The tangent components of flux lines 10 make no contribution to the creation of eddy currents. If the surface of the conductor 18 were tangent to flux lines 10, then only tangent components would be present, and there would be no normal component to the magnetic flux, and consequently no eddy currents would be induced.

Figure 2:
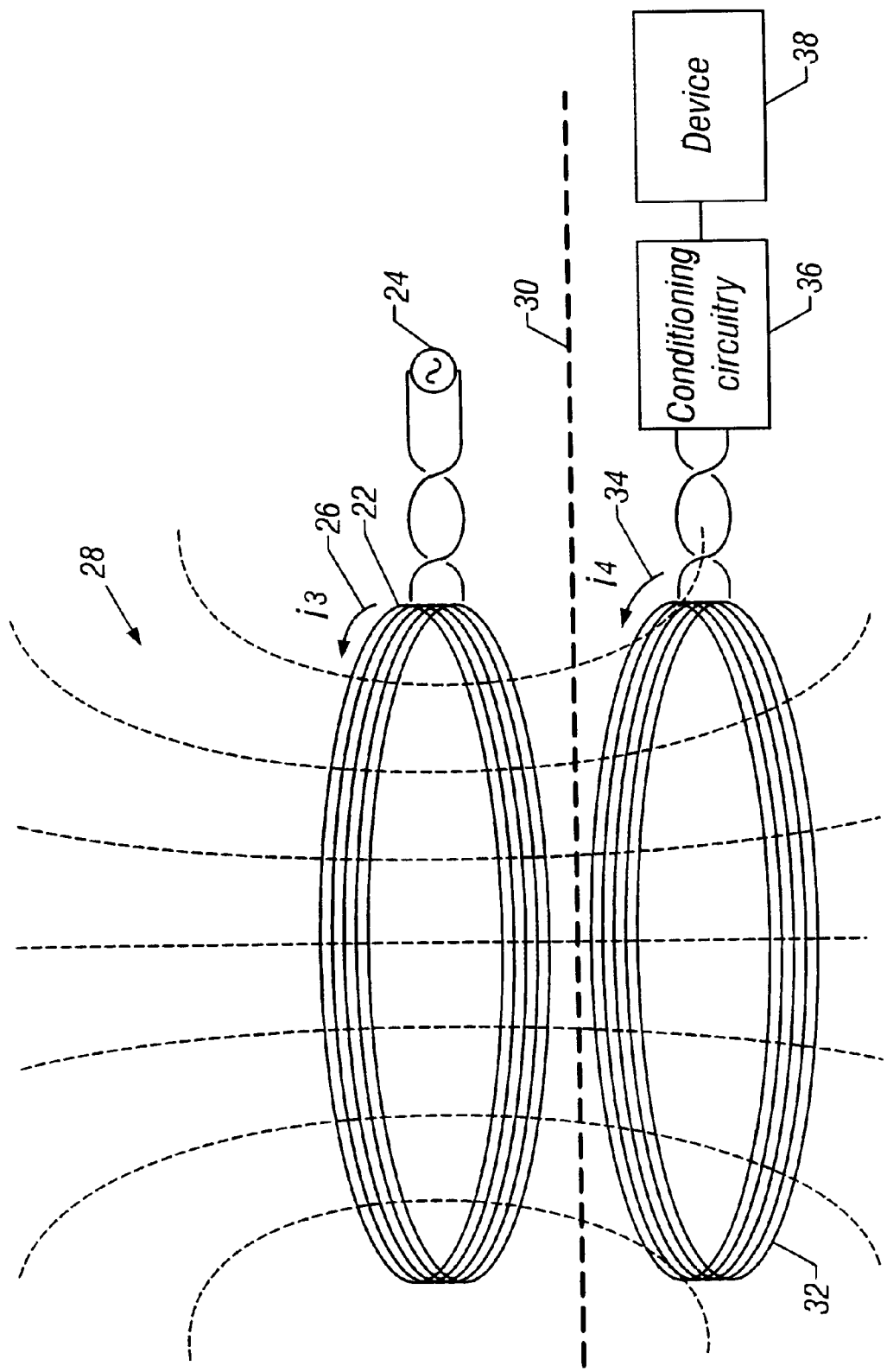
FIG. 2 is a simplified conceptual diagram of a two-coil configuration illustrating transcutaneous energy transfer by mutual induction.

FIG. 2 is a conceptual diagram depicting a two-coil configuration and block diagram illustrating transfer of power through a tissue barrier 30 by mutual induction. A time-varying current i3 (26) is generated in a primary closely-wound coil 22 by a source 24, creating time-varying magnetic flux 28. Magnetic flux 28 may pass through tissue barrier 30 and may encounter a secondary, subcutaneous closely-wound coil 32. For ease of representation, primary coil 22 and secondary coil 32 are not depicted in FIG. 2 as closely-wound. Secondary coil 32 is implanted beneath tissue barrier 30. Magnetic flux 28 inductively couples primary coil 22 and secondary coil 32. As magnetic flux 28 changes, a time-varying current i4 (34) is induced in secondary coil 32.

The induced current i4 (34) represents a time-varying or alternating current (ac) signal that may be conditioned by conditioning circuitry 36. Conditioning circuitry 36 is ordinarily electrically coupled to secondary coil 32. Conditioning may include, for example, rectification of the signal, filtering of the signal, and regulation of voltage or current levels. Currents and voltages conditioned by conditioning circuitry 36 may then be used by subcutaneous electrical device 38, which is electrically coupled to conditioning circuitry 36 and is implanted beneath tissue barrier 30.

Although not shown in FIG. 2, conditioning circuitry 36 may be electrically coupled to a control module that drives the device. In FIG. 2, conditioning circuitry 36 is depicted for ease of representation as a block outside the perimeter of secondary coil 32. To save space and to make conditioning circuitry 36 more easily implantable, it may be advantageous physically to place the conditioning circuitry inside the perimeter, within the aperture of secondary coil 32. Typically secondary coil 32 will be encapsulated in a casing of biocompatible material such as silicone prior to implantation, and placing conditioning circuitry 36 within the aperture of secondary coil 32 will allow the conditioning circuitry to be mounted within the aperture and to be encapsulated as well.

Conditioning circuitry 36 may consist of electrical elements such as diodes, transistors, capacitors and resistors selected to convert the ac power from secondary coil 32 to dc power. Such circuitry can ordinarily be constructed in a substantially planar fashion, using conducting and semiconducting materials. The circuitry may take the form of a contiguous circuit package that includes the various electrical elements, and includes at least one terminal coupled to secondary coil 32 and at least one other terminal coupled to the control module of device 38. The dc power then is transmitted from conditioning circuitry 36 to a control module that drives implantable device 38.

FIG. 2 illustrates one kind of transcutaneous energy transfer system. In FIG. 2, energy consumed by subcutaneous electrical device 38 is supplied from outside tissue barrier 30 by source 24. The energy is transferred through tissue barrier 30 by way of inductive coupling between primary coil 22 and secondary coil 32. It may also be said that the power, or energy per unit time, consumed by subcutaneous electrical device 38 is supplied from outside the skin by source 24.

Figure 3B:
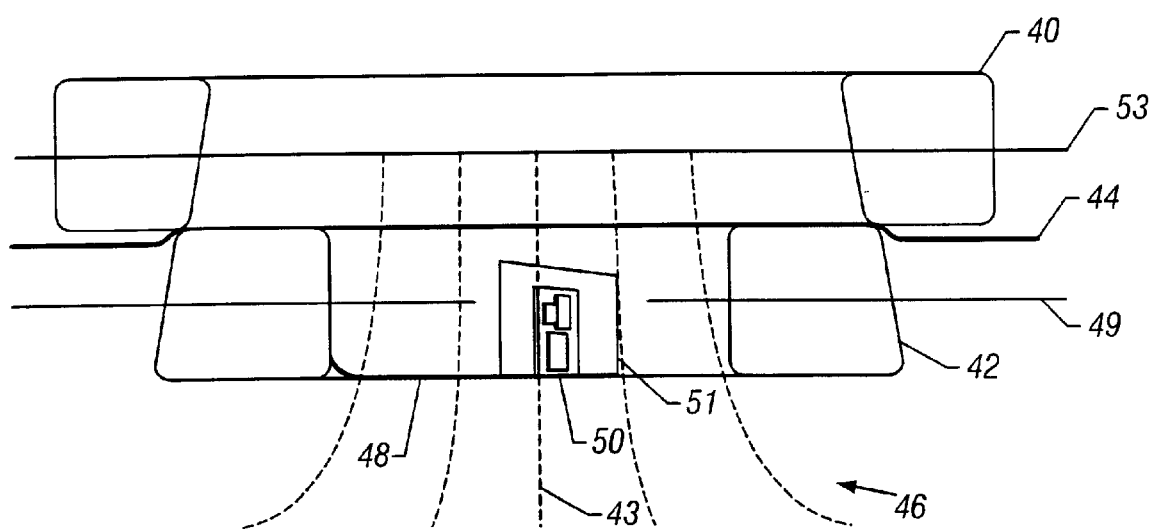
FIG. 3B is a cross-sectional view of two coils and an a power conditioning circuit board in accordance with an embodiment of the invention.
Figure 3A:
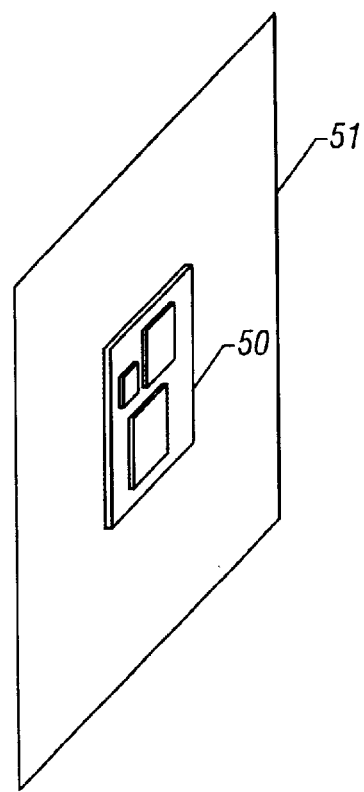
FIG. 3A is a perspective diagram of a power conditioning circuit board.

FIG. 3A is a perspective drawing of power conditioning circuitry 50. As shown in FIG. 3A, circuitry 50 has been constructed in a substantially planar fashion, and defines a major circuit plane 51. Most of the conducting materials in conditioning circuitry 50 lie coincident with, tangent to or parallel to major circuit plane 51. FIG. 3B is a cross-sectional view of a primary coil 40 and a secondary coil 42. Secondary coil 42 is implanted beneath the tissue barrier 44. The sizes and shapes of primary coil 40 and secondary coil 42 may vary.

As shown in FIG. 3B, the axes 43 of primary coil 40 and secondary coil 42 coincide. A coil configuration in which the axes of the coils substantially coincide is called a "coaxial" configuration. As shown in FIG. 3B, the major coil plane 53 of primary coil 40 is approximately parallel to tissue barrier 44, and is also approximately parallel to the major coil plane 49 of secondary coil 42. In addition, axes 43 of both coils 40, 42 are approximately perpendicular to tissue barrier 44 and to major coil planes 53, 49. If secondary coil 42 is substantially circular, major circuit plane 51 may be approximately aligned with a diameter of secondary coil 42, substantially perpendicular to major coil plane 49 of secondary coil 42. Furthermore, conditioning circuitry 50 may be located near the center of the aperture of secondary coil 42.

Conditioning circuitry 50 shown inside the aperture of secondary coil 42 in FIG. 3B is the same as conditioning circuitry 50 shown in FIG. 3A. Conditioning circuitry 50 is electrically coupled to secondary coil 42 by leads 48. One or more leads (not shown in FIG. 3B) may electrically couple circuitry 50 to a subcutaneous electrical device (not shown in FIG. 3B). Conditioning circuitry 50 holds a substantially fixed position relative to secondary coil 42, and may be mounted within secondary coil 42 in many ways, such as by encapsulation within a casing of biocompatible material such as silicone. The magnetic flux lines 46 generated by passing current through primary coil 40 are generally parallel to coil axes 43 and are generally perpendicular to major coil plane 49 of secondary coil 42, especially near the center of the aperture of secondary coil 42.

In the example of FIG. 3B, major circuit plane 51 of conditioning circuitry 50 has been oriented to be substantially parallel to coil axes 43 and perpendicular to the major coil plane 49 of secondary coil 42. Such orientation places major circuit plane 51 of conditioning circuitry 50 substantially tangent to the magnetic flux lines 46 that conditioning circuitry 50 may encounter while current is passed through primary coil 40. By being oriented substantially tangent to magnetic flux lines 46, eddy currents within conditioning circuitry 50 are minimized. Consequently, undesirable heating and energy loss due to eddy currents within conditioning circuitry 50 are minimized.

It is understood that circuitry, in place of or in addition to that related to conditioning the ac signal, may be oriented within the coil in a similar manner. It is also understood that conductive materials unrelated to circuitry may be so oriented so as to minimize eddy currents and attendant heat.

In some circumstances, available space considerations or other considerations may make it difficult to place all of the conditioning circuitry in a single plane. There are many possible arrangements by which the circuitry may be oriented so as to minimize eddy currents. One such example appears in FIG. 4. FIG. 4 is a perspective view of conditioning circuitry 52 in which circuitry has been divided into two planar subcircuits 54, 56. Planar subcircuits 54, 56 may be stacked in a "double-decker" fashion and may be connected by leads 58. When placed in a secondary coil such as secondary coil 42 shown in FIG. 3B, the plane of each subcircuit may be substantially tangent to the lines of magnetic flux. In a similar manner, an additional subcircuit could be added, with the subcircuits stacked in "triple-decker" fashion. Any number of subcircuits may be coupled in this way, each subcircuit substantially tangent to the lines of magnetic flux.

Another example of arrangement of circuitry appears in FIG. 5, in which circuitry 60 is distributed among a plurality of planar subcircuits, each of which may be oriented within a secondary coil substantially tangent to the lines of magnetic flux. As shown in FIG. 5, the subcircuits need not be stacked as shown in FIG. 4. Instead, the subcircuits may be arranged with interlocking circuit planes.

A further example of arrangement of circuitry appears in FIG. 6, in which the circuitry 62 is not strictly planar. As shown in FIGS. 1, 2 and 3B, lines of magnetic flux are not necessarily straight. Therefore, circuitry may be applied to a curved surface that may still be substantially tangent to the lines of magnetic flux. Although the circuitry as a whole may be curved, locally the circuitry is substantially planar and substantially tangent to the lines of magnetic flux.

The arrangements shown in FIGS. 4, 5 and 6 are merely exemplary. There are an infinite number of ways to arrange the circuitry to make it substantially tangent to the lines of magnetic flux. A circuit designer wishing to reduce the profile of the circuitry may employ any number of ways to distribute the electrical components necessary for conditioning among two or more circuit planes. Each circuit plane may then be positioned to make the plane substantially tangent to the lines of magnetic flux.

Alternatively, the designer may distribute the electrical components along one or more curved surfaces, with each surface positioned to make the circuitry locally substantially tangent to the lines of magnetic flux. The present invention has the advantage of flexibility of circuit design, whereby the circuit designer has a wide range of options for arrangement of circuit elements to save space or to reduce the profile of the circuitry. The present invention has the further advantage of reducing the effects of eddy currents within the circuitry, thereby helping avoid generation of excess heat.

In FIGS. 2 and 3B, the primary and secondary coils are depicted as simple coaxial coils. The depiction is for illustration only, and the present invention may have a far wider-ranging application. For example, the coils need not be comparably sized, as depicted in FIG. 2. One coil may have a substantially larger radius than the other, and instead of placing the coils one atop the other, the coils may be placed one inside the other, assuming the tissue barrier is sufficiently deformable to permit such an arrangement. In this arrangement, the coils share substantially the same major plane and the same axis.

Furthermore, the coils need not be in a coaxial configuration, which is only one of many configurations that may be used for transcutaneous energy transfer. In addition to the positions and sizes of the coils, other TETS configurations may include cores within the coils, or may have the coils wound in a solenoid-like fashion, or may have coils composed of various kinds of wire. There may also be a multitude of ways for tuning the coils for maximum efficient energy transfer, or for applying particular current oscillations.

Although there may be a wide assortment of configurations used for TETS, many configurations for TETS involve magnetic flux, and may have the potential to create undesirable eddy currents. The present invention, relating to orientation of the conditioning circuitry to make the circuitry substantially tangent to the lines of magnetic flux, may be applied to these other TETS configurations.

The foregoing detailed description has been provided for a better understanding of the invention and is for exemplary purposes only. Modifications may be apparent to those skilled in the art, however, without deviating from the spirit and scope of the appended claims. Other embodiments are within the scope of the following claims.

What is claimed is:

1. A device for use in transcutaneous energy transfer, comprising:

a coil for subcutaneous placement within a human, and circuitry that is electrically connected to the coil, and configured to conduct current induced in the coil, wherein a major plane of the circuitry is oriented substantially perpendicular to a major plane of the coil, thereby reducing the generation of eddy currents within the circuitry while current is conducting in the coil.

2. The device of claim 1, further comprising a casing composed of biocompatible material encapsulating the coil and the circuitry.

3. The device of claim 1, wherein the circuitry is located within the aperture of the coil.

4. The device of claim 1, further comprising leads permitting attachment to a subcutaneous electrical device.

5. The device of claim 1, wherein the shape of the coil is substantially circular.

6. The device of claim 1, wherein the circuitry is located near the axis of the coil.

7. The device of claim 1, wherein the circuitry consists of substantially planar subcircuits, the planes of the subcircuits are substantially located perpendicular to the major plane of the coil.

8. The device of claim 1, wherein the circuitry consists of planar subcircuits, the subcircuits being electrically coupled by leads, and the major planes of the subcircuits being substantially parallel to each other.

9. The device of claim 1, wherein the coil is a secondary coil, and wherein the lines of magnetic flux are principally generated by a primary coil external to the skin.

10. The device of claim 9, wherein the substantially planar circuitry is oriented substantially tangent to the lines of magnetic flux generated by the primary coil.

11. The device of claim 9, wherein the substantially planar circuitry is curved such that the local plane of the circuitry is oriented substantially tangent to the lines of magnetic flux generated by the primary coil.

12. The device of claim 9, wherein the primary coil and the secondary coil are arranged coaxially.

13. A transcutaneous energy transfer system, comprising a primary coil for placement external to the skin, the coil suitable for carrying a time-varying current, a current source arranged in series with the primary coil, comprising a power supply and power circuitry capable of delivering an electric current to the primary coil to produce magnetic flux, a secondary coil for subcutaneous placement, the coil suitable for carrying a current induced by the magnetic flux, and substantially planar conditioning circuitry that is electrically coupled to the secondary coil and conducts current induced in the secondary coil, wherein the plane of the conditioning circuitry is oriented substantially perpendicular to the a major plane of the secondary coil.

14. The system of claim 13, wherein the conditioning circuitry performs at least one of the functions of rectification, filtering and regulation.

15. The system of claim 13, further comprising:

a subcutaneous electrical device, and leads permitting electrical coupling of the conditioning circuitry to the subcutaneous electrical device.

16. The system of claim 15, wherein the subcutaneous electrical device comprises an implantable blood pump.

17. The system of claim 15, wherein the subcutaneous electrical device comprises an electrical storage battery.

18. The system of claim 13, wherein the conditioning circuitry is located within the aperture of the secondary coil.

19. The system of claim 13, wherein the primary and secondary coils are arranged coaxially.

20. The system of claim 13, wherein the shape of the primary coil is substantially circular and the shape of the secondary coil is substantially circular.

21. The system of claim 13, wherein the plane of the conditioning circuitry is located substantially perpendicular to the major plane of the primary coil.

22. The system of claim 13, wherein the conditioning circuitry is oriented to reduce eddy currents induced by the magnetic flux.

23. The system of claim 13, wherein the conditioning circuitry comprises two or more electrically coupled substantially planar subcircuits, the plane of the subcircuits being oriented substantially perpendicular to the a major plane of the secondary coil.

24. The system of claim 13, wherein the conditioning circuitry comprises two or more electrically coupled subcircuits, the subcircuits being oriented to reduce eddy currents induced by the magnetic flux.

25. A method for delivering energy transcutaneously, the method comprising:

placing a primary coil external to the skin, the primary coil being electrically coupled to a power supply capable of delivering time-varying current to the primary coil, determining the orientation of magnetic flux lines principally caused by time-varying current circulating in the primary coil, constructing conditioning circuitry in substantially planar fashion, and placing a secondary coil beneath the skin, the secondary coil being electrically connected to the conditioning circuitry and the conditioning circuitry oriented substantially tangent to the lines of magnetic flux.

26. The method of claim 25, further comprising dividing the conditioning circuitry into subcircuits, each subcircuit being substantially planar;

electrically coupling the subcircuits, and orienting the planes of the subcircuits within the aperture of the secondary coil substantially parallel to the lines of magnetic flux.

27. The method of claim 26, further comprising placing the planes of the subcircuits in a substantially parallel stacked configuration.

28. The method of 25, further comprising encapsulating the secondary coil and the conditioning circuitry within a casing composed of biocompatible material.

* * * * *